(12) United States Patent
Canady et al.

(10) Patent No.: US 10,770,271 B2
(45) Date of Patent: *Sep. 8, 2020

(54) PLASMA-ACTIVATED SALINE SOLUTIONS AND METHOD OF MAKING PLASMA ACTIVATED SALINE SOLUTIONS

(71) Applicant: U.S. Patent Innovations LLC, Takoma Park, MD (US)

(72) Inventors: Jerome Canady, Lakeland, FL (US); Michael Keidar, Baltimore, MD (US); Zhitong Chen, Ashburn, VA (US)

(73) Assignee: U.S. Patent Innovations LLC, Takoma Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/298,484

(22) Filed: Mar. 11, 2019

(65) Prior Publication Data
US 2019/0279849 A1 Sep. 12, 2019

Related U.S. Application Data

(60) Provisional application No. 62/640,886, filed on Mar. 9, 2018.

(51) Int. Cl.
*H01J 37/32* (2006.01)
*A61K 35/08* (2015.01)
*A61P 35/00* (2006.01)

(52) U.S. Cl.
CPC ........ *H01J 37/32825* (2013.01); *A61K 35/08* (2013.01); *H01J 37/32366* (2013.01); *H01J 37/32422* (2013.01); *H01J 37/32568* (2013.01); *A61P 35/00* (2018.01)

(58) Field of Classification Search
CPC .......... H01J 37/32568; H01J 37/32366; H01J 37/32422; A61K 35/08; A61P 35/00
See application file for complete search history.

(56) References Cited

U.S. PATENT DOCUMENTS

| 9,999,462 B2 | 6/2018 | Canady et al. |
| 10,213,614 B2 | 2/2019 | Keidar et al. |

FOREIGN PATENT DOCUMENTS

WO 2018191265 A1 10/2018

OTHER PUBLICATIONS

Chen et al. ("In vitro Demonstration of Cancer Inhibiting Properties From Stratified Self-Organized Micro-Discharge Plasma-Lioquid Interface," pp. 1-17, 2017.*

(Continued)

*Primary Examiner* — Blessing M Fubara
(74) *Attorney, Agent, or Firm* — 24IP Law Group USA, PLLC (57) ABSTRACT

A method for manufacturing plasma-activated saline for treatment of cancer cells. The method comprises the steps of immersing a cathode in saline solution in a container, positioning an anode at a fixed distance from a surface of said saline solution in said container and applying electrical energy to said anode for a fixed period of time, wherein said fixed distance and said fixed period of time are selected to cause a plasma self-organized pattern at a surface of said saline solution with an atmospheric discharge between said anode and said cathode.

7 Claims, 4 Drawing Sheets

(56) References Cited

OTHER PUBLICATIONS

Radehaus, C., Dirksmeyer, T., Willebrand, H. & Purwins, H.-G. Pattern formation in gas discharge systems with high impedance electrodes. Physics Letters A 125, 92-94 (1987).

Trelles, J. P. Formation of self-organized anode patterns in arc discharge simulations. Plasma Sources Science and Technology 22, 025017 (2013).

Kogelschatz, U. Filamentary, patterned, and diffuse barrier discharges. IEEE Transactions on plasma science 30, 1400-1408 (2002).

Shirai, N., Ibuka, S. & Ishii, S. Atmospheric DC glow discharge observed in intersecting miniature gas flows. IEEE Transactions on Plasma Science 36, 960-961 (2008).

Laroussi, M., Lu, X. & Malott, C. M. A non-equilibrium diffuse discharge in atmospheric pressure air. Plasma Sources Science and Technology 12, 53 (2003).

André, P. et al. Experimental study of discharge with liquid non-metallic (tap-water) electrodes in air at atmospheric pressure. Journal of Physics D: Applied Physics 34, 3456 (2001).

Chen, Z., Zhang, S., Levchenko, I., Beilis, I. I. & Keidar, M. In vitro Demonstration of Cancer Inhibiting Properties from Stratified Self-Organized Micro-Discharge Plasma-Liquid Interface. arXiv preprint arXiv:1701.01655 (2017).

Benilov, M. Bifurcations of current transfer through a collisional sheath with ionization and self-organization on glow cathodes. Physical Review E 77, 036408 (2008).

Shirai, N., Uchida, S. & Tochikubo, F. Influence of oxygen gas on characteristics of self-organized luminous pattern formation observed in an atmospheric dc glow discharge using a liquid electrode. Plasma Sources Science and Technology 23, 054010 (2014).

Shirai, N., Ibuka, S. & Ishii, S. Self-organization pattern in the anode spot of an atmospheric glow microdischarge using an electrolyte anode and axial miniature helium flow. Applied Physics Express 2, 036001 (2009).

Ostrikov, K. K., Cvelbar, U. & Murphy, A. B. Plasma nanoscience: setting directions, tackling grand challenges. Journal of Physics D: Applied Physics 44, 174001 (2011).

Kong, M. G. et al. Plasma medicine: an introductory review. new Journal of Physics 11, 115012 (2009).

\* cited by examiner

PLASMA-ACTIVATED SALINE SOLUTIONS AND METHOD OF MAKING PLASMA ACTIVATED SALINE SOLUTIONS

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

Field of the Invention

The present invention relates to methods of cancer treatment.

Brief Description of the Related Art

Self-organization is generally referred to as a process of spontaneous transition from a homogeneous stable state to a regular pattern in a spatially extended system. See, Radehaus, C., Dirksmeyer, T., Willebrand, H. & Purwins, H.-G. Pattern formation in gas discharge systems with high impedance electrodes. *Physics Letters A* 125, 92-94 (1987) and Jager, D., Baumann, H. & Symanczyk, R. Experimental observation of spatial structures due to current filament formation in silicon pin diodes. *Physics Letters A* 117, 141-144 (1986). Self-organization is a complex and fascinating phenomenon commonly observed in both natural and technological contexts within diverse varieties of physics, chemistry and biology. Raizer, Y. P. & Mokrov, M. Physical mechanisms of self-organization and formation of current patterns in gas discharges of the Townsend and glow types. *Physics of Plasmas* 20, 101604 (2013) and Trelles, J. P. Formation of self-organized anode patterns in arc discharge simulations. *Plasma Sources Science and Technology* 22, 025017 (2013). Different types of self-organization phenomena have been reported in a wide range of plasmas, such as dielectric barrier discharge (see, Kogelschatz, U. Filamentary, patterned, and diffuse barrier discharges. *IEEE Transactions on plasma science* 30, 1400-1408 (2002)), high frequency discharge (see, Shi, J., Liu, D. & Kong, M. G Plasma stability control using dielectric barriers in radio-frequency atmospheric pressure glow discharges. *Applied physics letters* 89, 081502 (2006)), gas flow stabilized discharges (see, Akishev, Y. et al. The influence of electrode geometry and gas flow on corona-to-glow and glow-to-spark threshold currents in air. *Journal of Physics D: Applied Physics* 34, 2875 (2001) and Shirai, N., Ibuka, S. & Ishii, S. Atmospheric DC glow discharge observed in intersecting miniature gas flows, *IEEE Transactions on Plasma Science* 36, 960-961 (2008)), resistively stabilized discharged (see, Laroussi, M., Alexeff, I., Richardson, J. P. & Dyer, F. F. The resistive barrier discharge. *IEEE Transactions on Plasma Science* 30, 158-159 (2002)), and discharges with liquid electrodes (see, Laroussi, M., Lu, X. & Malott, C. M. A non-equilibrium diffuse discharge in atmospheric pressure air. *Plasma Sources Science and Technology* 12, 53 (2003), André, P. et al. Experimental study of discharge with liquid non-metallic (tap-water) electrodes in air at atmospheric pressure. *Journal of Physics D: Applied Physics* 34, 3456 (2001) and Chen, Z., Zhang, S., Levchenko, I., Beilis, I. I. & Keidar, M. In vitro Demonstration of Cancer Inhibiting Properties from Stratified Self-Organized Micro-Discharge Plasma-Liquid Interface. *arXiv preprint arXiv*:1701.01655 (2017)). The self-organization phenomena associated with the formation of electrode patterns are significantly different among these discharges, which typically occur in the anode or cathode layer. Benilov, M. Bifurcations of current transfer through a collisional sheath with ionization and self-organization on glow cathodes. *Physical Review E* 77, 036408 (2008) and Schoenbach, K. H., Moselhy, M. & Shi, W. Self-organization in cathode boundary layer microdischarges. *Plasma Sources Science and Technology* 13, 177 (2004). Self-organization patterns ($SOP_S$) of plasma include square-textures, square-lattices, square/hexagonal superlattices, hollow-hexagonal, multi-armed spirals, rotating-wheels patterns, etc. Dong, L., Fan, W., He, Y. & Liu, F. Self-organized gas-discharge patterns in a dielectric-barrier discharge system. *IEEE Transactions t Plasma Science* 36, 1356-1357 (2008) and Dong, L. et al. Collective vibration of discharge current filaments in a self-organized pattern within a dielectric barrier discharge. *Physical Review E* 85, 066403 (2012). The formation of these patterns depends on various parameters such as driving current, electrolyte conductivity, gap length, gas species, and so on. See, Shirai, N., Uchida, S. & Tochikubo, F. Influence of oxygen gas on characteristics of self-organized luminous pattern formation observed in an atmospheric dc glow discharge using a liquid electrode. *Plasma Sources Science and Technology* 23, 054010 (2014), Shirai, N., Ibuka, S. & Ishii, S. Self-organization pattern in the anode spot of an atmospheric glow microdischarge using an electrolyte anode and axial miniature helium flow. *Applied Physics Express* 2, 036001 (2009) and Zheng, P. et al. Self-organized pattern formation of an atmospheric-pressure, ac glow discharge with an electrolyte electrode. *Plasma Sources Science and Technology* 24, 015010 (2014). Recently, plasma discharges with the liquid electrode have been studied referring to applications ranging from water decontamination and activation (see, Locke, B., Sato, M., Sunka, P., Hoffmann, M. & Chang, J.-S. Electrohydraulic discharge and nonthermal plasma for water treatment. *Industrial & engineering chemistry research* 45, 882-905 (2006) and Ostrikov, K. K., Cvelbar, U. & Murphy, A. B. Plasma nanoscience: setting directions, tackling grand challenges. *Journal of Physics D: Applied Physics* 44, 174001 (2011)), to nanoparticle and materials synthesis (Ostrikov, K. K., Cvelbar, U. & Murphy, A. B. Plasma nanoscience: setting directions, tackling grand challenges. *Journal of Physics D: Applied Physics* 44, 174001 (2011) and Richmonds, C. & Sankaran, R. M. Plasma-liquid electrochemistry: rapid synthesis of colloidal metal nanoparticles by microplasma reduction of aqueous cations. *Applied Physics Letters* 93, 131501 (2008)), and medicine (see, Kong, M. G. et al. Plasma medicine: an introductory review. new *Journal of Physics* 11, 115012 (2009)). Therefore, self-organization in plasma interacting with surfaces is interest not only from a fundamental point of view as intrinsic and fascinating characteristics of nature, but also from practical standpoint in current and emerging technological applications.

SUMMARY OF THE INVENTION

The present invention creates plasma with different self-organization patterns (SOPs) to activate saline solution. The plasma activated saline solutions have anti-tumor effects on human pancreatic normal and cancer cells.

In a preferred embodiment, the present invention is a method for manufacturing plasma-activated saline for treatment of cancer cells. The method comprises the steps of immersing a cathode in saline solution in a container, positioning an anode at a fixed distance from a surface of said saline solution in said container and applying electrical energy to said anode for a fixed period of time, wherein said fixed distance and said fixed period of time are selected to cause a plasma self-organized pattern at a surface of said saline solution with an atmospheric discharge between said anode and said cathode. The fixed distance typically is 2-8 mm and preferably may be 4-6 mm. The fixed time may be, for example, 40 seconds. The produced plasma self-organized pattern preferably comprises a double ring structure, which may be a solid inner ring surrounded by a continuous or discontinuous outer ring or a continuous inner ring surrounded by a continuous or discontinuous outer ring. A discontinuous outer ring of a double ring pattern may be, for example, a plurality of dots forming a discontinuous ring.

In another embodiment, the present invention is a method for treatment of cancer cells. The method comprises immersing a cathode in saline solution in a container, positioning an anode at a distance from a surface of said saline solution in said container, applying electrical energy to said anode for a period of time to create a plasma self-organized pattern at a surface of said saline solution with an atmospheric discharge between said anode and said cathode, and treating human cancer cells with said plasma activated saline solution. The step of treating human cancer cells with said plasma activated saline solution may comprise injecting said plasma activated saline solution into an area of a human body containing said human cancer cells. The human cancer cells comprise human pancreas adenocarcinoma cancer cells. The distance between the cathode and the surface of the saline solution in the container may be 2-8 mm and preferably is 4-6 mm. The period of time may be, for example, 40 seconds. The produced plasma self-organized pattern preferably comprises a double ring structure, which may be a solid inner ring surrounded by a continuous or discontinuous outer ring or a continuous inner ring surrounded by a continuous or discontinuous outer ring. A discontinuous outer ring of a double ring pattern may be, for example, a plurality of dots forming a discontinuous ring.

In another embodiment, the present invention is a method for manufacturing plasma-activated saline for treatment of cancer cells. The method comprises generating with an atmospheric discharge between an anode and a cathode a plasma self-organized pattern at a surface of saline solution, wherein the anode is submersed in the saline solution and the cathode is at a distance from the surface of the saline solution and a plasma is formed in a gap between said cathode and said surface of said saline solution, and maintaining said atmospheric discharge for a period of time greater than 10 seconds, wherein said self-organized pattern is a double ring.

Plasma interacting with the liquid generates reactive oxygen species (ROS) and reactive nitrogen species (INS) that act as key intermediate for cancer therapy. See, Boehm, D., Heslin, C., Cullen, P. J. & Bourke, P. Cytotoxic and mutagenic potential of solutions exposed to cold atmospheric plasma. *Scientific reports* 6 (2016); Chen, Z. et al. A Novel Micro Cold Atmospheric Plasma Device for Glioblastoma Both In Vitro and In Vivo. *Cancers* 9, 61 (2017). The present invention creates plasma with different self-organization patterns (SOPs) to activate saline solution. The plasma activated saline solutions have anti-tumor effects on human pancreatic normal and cancer cells. A camera was used to characterize the patterns of plasma with SOP. The spectra of plasma with SOPs were determined by UV-visible-NIR optical emission spectroscopy OES). The concentration of hydrogen peroxide ($H_2O_2$) and nitrite ($NO_2^-$) was measured by using a Fluorimetric hydrogen peroxide assay kit, and the Griess reagent system, respectively. The cell viability of H6c7 and BxPC-3 was measured via Cell Counting KIT 8 Assay. Typically, saline solution is used to treat dehydration by injection into a vein, and it is also used to dilute medications to be given by injection. Based on the results, one can suggest that SOP plasma-activated saline solutions (plasma solutions) has the potential to be utilized as an oral medicine or drug injected into tumors.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 5A and 5B show effects of seven media: RPMI/KSFM, saline solution (SS), and five plasma-activated media (saline solution activated by plasma with SOP at 2, 4, 6, 8, and 10 mm distance for 40 seconds' treatment) on viability of the BxPC-3 human pancreas cancer cells d the H6c7 human pancreas normal cells after 24 (a) and 48 (b)

hours' incubation, respectively. The percentages of surviving cells for each cell line were calculated relative to controls (RPMI/KSFM).

DETAILED DESCRIPTION OF THE PREFERRED EMBODIMENTS

The preferred embodiments of the invention and the experiments will be described with reference to the drawings.

Figure 1:
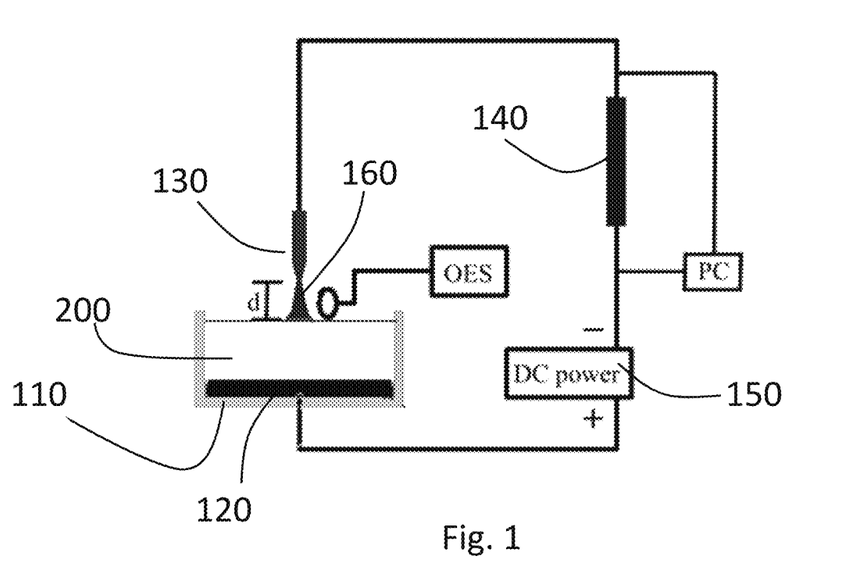
FIG. 1 shows a schematic representation of the SOP plasma discharge setup capable of producing well-defined self-organized interface patterns at the surface of the liquid/plasma interface. Different air gap distances between the cathode and surface of liquid accommodated plasma. (d is the distance of air gap).
Figure 2A:
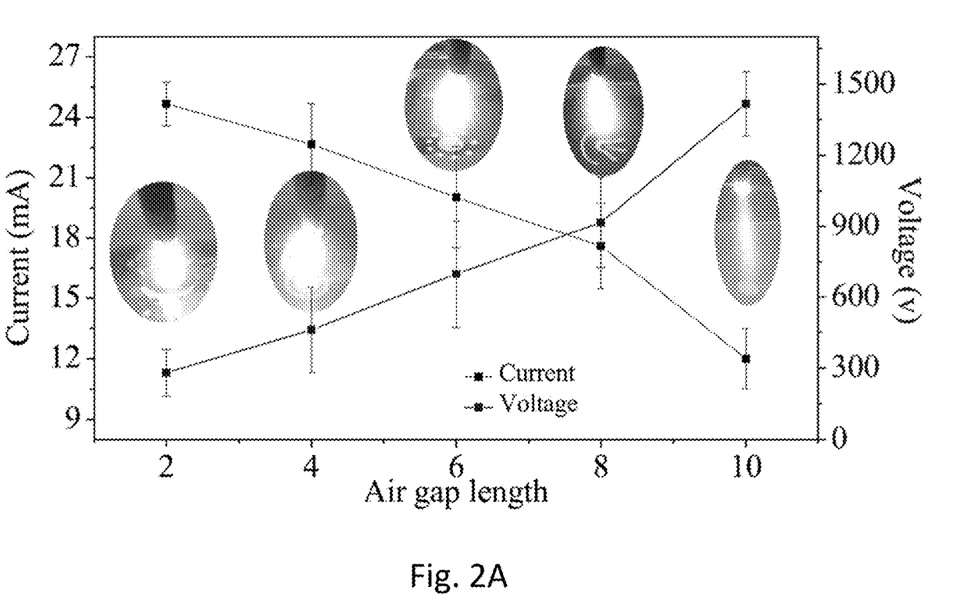
FIG. 2A illustrate a current-voltage dependence for different air gap lengths with optical photographs of the self-organized stratified interface patterns.
Figure 2B:
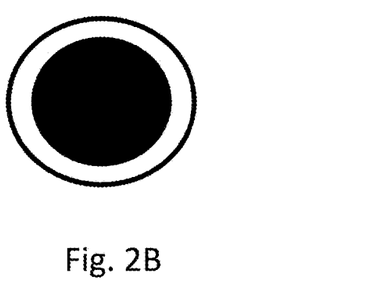
FIG. 2B is a diagram of a double ring self-organized pattern with a solid inner ring and a continuous outer ring in accordance with a preferred embodiment of the present invention.
Figure 2C:
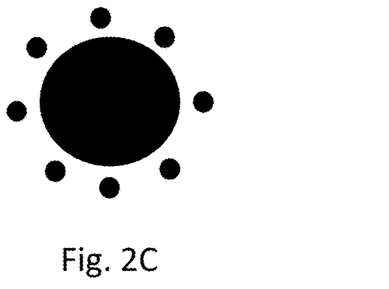
FIG. 2C is a diagram of a double ring self-organized pattern with a solid inner ring and a discontinuous outer ring in accordance with another preferred embodiment of the present invention.
Figure 3A:
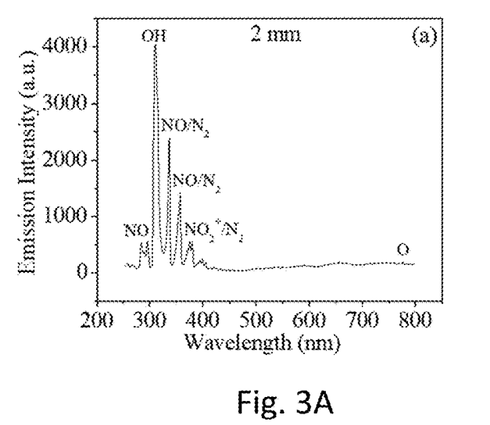
FIGS. 3A-3E show the Optical emission spectrum by the SOP plasma discharge above saline solution with different air gap length taken using UV-visible-NIR in the 200-850 nm wavelength range: (a) 2 mm, (b) 4 mm, (c) 6 mm, (d) 8 mm, and (e) 10 mm.
Figure 3B:
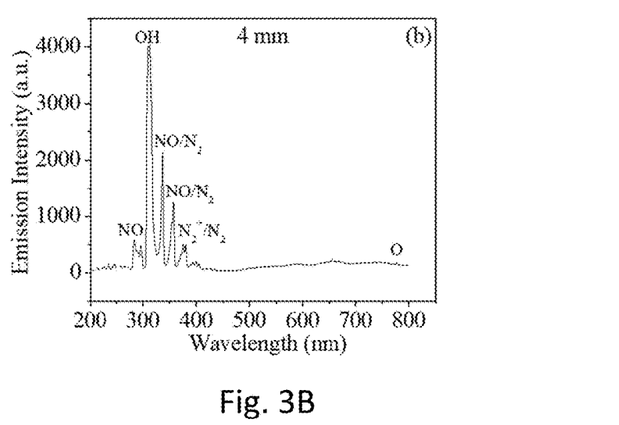
Figure 3C:
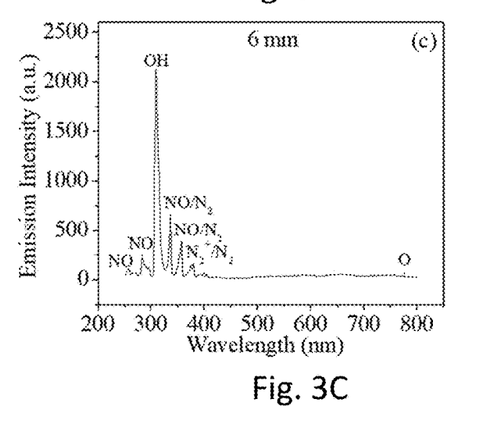
Figure 3D:
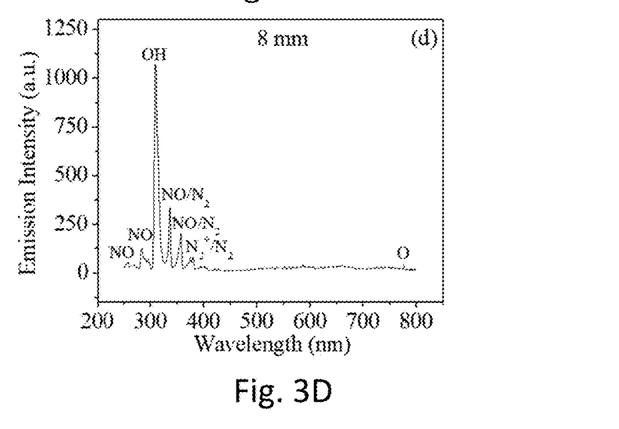
Figure 3E:
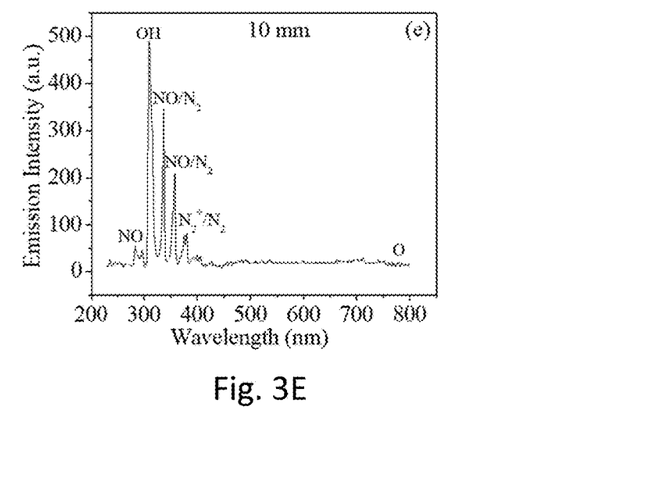

FIG. 1A shows a schematic representation of a self-organized pattern plasma discharge setup capable of producing well-defined self-organized interface patterns at the surface of a liquid/plasma interface. An anode 120 (a thin copper plate, thickness d=0.2 mm, Ø=22 mm) is placed at the bottom of a glass-made well 110. A saline solution 200 is placed in the glass well. A tungsten cathode 130 of Ø=2 mm is then installed above the saline solution surface. A ballast resistor 140 (90 KΩ) is connected between the cathode 130 and a direct current (DC) power supply unit 150 (Power Design, Model 1570A, 1-3012V, 40 mA). A voltage is applied between the cathode 130 and the liquid-immersed anode 120, and a plasma 160 is formed in a small (2-10 mm) gap between the cathode and liquid surface accommodated. As shown in FIG. 2A, voltage of 300-1500 v were applied with currents of approximately 10-25 mA.

In a series of experiments, saline solution was treated by discharge with a 2, 4, 6, 8, and 10 mm air gap length d between the cathode 130 and the surface of the plasma 200 to obtain plasma-activated solutions for treating cancer cells.

A. Cell Cultures for the Experiments

The human pancreas adenocarcinoma cancer cell line (BxPC-3) was acquired from American Type Culture Collection (ATCC). Cell lines were cultured in RPMI-1640 Medium (ATCC® 30-2001™) supplemented with 10% (v/v) fetal bovine serum (Atlantic Biologicals) and 1% (v/v) penicillin and streptomycin (Life Technologies). The human pancreatic duct epithelial normal cell line (H6c7, Kerafast) was cultured in Keratinocyte SFM (KSFM, Gibco) supplemented with prequalified human recombinant Epidermal Growth Factor 1-53 (EGF 1-53, Gibco), Bovine Pituitary Extract (BPE, Gibco), and 1% (v/v) penicillin and streptomycin (Life Technologies). Cultures were maintained at 37° C. in a humidified incubator containing 5% (v/v) $CO_2$. Cultures were maintained at 37° C. in a humidified incubator containing 5% (v/v) $CO_2$.

B. Evaluation of Hydrogen Peroxide ($H_2O_2$) Concentration

Fluorimetric Hydrogen Peroxide Assay Kit (Sigma-Aldrich) was used for measuring the amount of $H_2O_2$ in saline solution. A detailed protocol can be found on the Sigma-Aldrich website. Briefly, we added 50 µl of standard curves samples, controls, and experimental samples (saline solution treated by SOP plasma with 2, 4, 6, 8, and 10 mm air gap) to the 96-well flat-bottom black plates, and then added 50 µl of Master Mix (including Red Peroxidase Substrate Stock, 20 units/mL Peroxidase Stock, and Assay Buffer) to each of wells. We incubated the plates for 20 min at room temperature protected from light on and measured fluorescence by Synergy H1 Hybrid Multi-Mode Microplate Reader at Ex/Em: 540/590 nm.

C. Evaluation of Nitrite ($NO_2^-$) Concentration

Nitrite level were determined by using the Griess Reagent System, including 50 ml Sulfanilamide Solution, 50 ml NED solution, and 1 ml Nitrite Standard, (Promega Corporation) according to the instructions provided by the manufacturer. Briefly, we added 50 µl of standard curves samples, controls, and experimental samples to the 96-well flat-bottom plates. Then dispense 50 µl of the Sulfanilamide Solution to all samples and incubate 5-10 minutes at room temperature. Finally, dispense 50 µl of the NED solution to all wells and incubate at room temperature 5-10 minutes. The absorbance was measured at 540 nm by Synergy H1 Hybrid Multi-Mode Microplate Reader.

D. Measurement of Cell Viability

The cells were plated in 96-well flat-bottom microplates at a density of 3000 cells per well in 70 µL of complete culture medium. Cells were incubated for 24 hours to ensure proper cell adherence and stability. Confluence of each well was confirmed to be at ~40%. 30 µl of RPMI, saline solution, and plasma-activated saline solutions were added to the corresponding cells. Cells were further incubated at 37° C. for 24 and 48 hours. The viability of the pancreas normal and cancer cells was measured with Cell Counting Kit 8 assay (Dojindo Molecular Technologies, MD). The original culture medium was aspirated and 10 µL of CCK 8 reagent was added per well. The plates were incubated for 3 hours at 37° C. The absorbance was measured at 450 nm by Synergy H1 Hybrid Multi-Mode Microplate Reader. We normalized data according to control group (RPMI for BxPC-3, and KSFM for H6c7). We calculated the mean and standard deviation independently.

E. Optical Emission Spectra Measurement

UV-visible-NIR, a range of wavelength 200-850 nm, was investigated on plasma to detect various RNS and ROS (nitrogen [$N_2$], nitric oxide [—NO], nitrogen cation [$N^{+2}$], atomic oxygen [O], and hydroxyl radical [—OH]). The spectrometer and the detection probe were purchased from Stellar Net Inc. The optical probe was placed 2 cm in front of the plasma beam. Integration time of the collecting data was set to 100 ms.

F. Statistical Analysis

All results were presented as mean±standard deviation plotted using Origin 8. Student's t-test was applied to check the statistical significance (*$p<0.05$, $p<0.01$, *$p<0.001$).

Results

A. Current-Voltage Characteristics of Discharge

FIG. 2A shows the current-voltage characteristics of the discharge with air gap at distance of 2-10 mm. With gap increasing, the discharge current decreases while discharge voltage increases. Similar features of the discharge voltage increasing with air gap length are found in the case of electrolyte anode/cathode discharge. See, Bruggeman, P. et al. DC excited glow discharges in atmospheric pressure air in pin-to-water electrode systems. *Journal of Physics D: Applied Physics* 41, 215201 (2008). The self-organized pattern appears at the plasma-liquid interface and the discharge is stabilized when the air gap length is about 6 mm. At 2 mm gap, the discharge voltage is low while discharge current is high, and the discharge pattern represents a single filament. As the air gap length increases from 2 mm to 4 mm, the anode spot changes to a double ring-like structure. At an air gap length of 4 mm, the double ring structure is a solid inner circle surrounded by a continuous outer circle. At an air gap length of 6 mm, the double ring structure is a solid inner circle surrounded by a discontinuous continuous outer circle formed of a plurality of circular dots. At air gap length of 8 mm, various types of self-organized patterns are formed above the liquid media surface as shown in FIG. 2A. When the air gap is 2 to 8 mm, the plasma discharge is stable. When the air gap is 10 mm however, the plasma discharge becomes unstable. If the air gap is larger than 10 mm, the plasma discharge cannot be sustained.

B. Optical Spectrum of SOP Plasma

We have measured spectra of plasma from the plasma-liquid interface. Typical optical emission spectra are shown in FIG. 3. One can see that with air gap length increasing, the emission intensity decreases. The identification of the emission bands was performed according to the reference. See, Pearse, R. W. B. & Gaydon, A. G. *Identification of molecular spectra*. (Chapman and Hall, 1976). In the 250-300 nm wavelength range, weak emission bands (258, 267, and 284) were detected as NO lines. See, Walsh, J. L. & Kong, M. G. Contrasting characteristics of linear-field and cross-field atmospheric plasma jets. *Applied Physics Letters* 93, 111501 (2008).

Species at wavelengths of 337 and 358 nm were defined as $N_2{}^3\Pi$ or $NO\ \beta^2\Pi$ (denoted as $N_2$/NO), because both species have possible optical emission at these wavelengths. See, Pearse, R. W. B. & Gaydon, A. G. *Identification of molecular spectra*. (Chapman and Hall, 1976). The emission bands between 300 and 500 nm have still not been clearly identified in the literature. See, Chen, W. et al. Treatment of *Enterococcus faecalis* bacteria by a helium atmospheric cold plasma brush with oxygen addition. *Journal of Applied Physics* 112, 013304 (2012). However, we anticipated that OH was present at 309 nm, the wavelength of 375 nm could be indicative of $N_2{}^+/N_2$, and atomic oxygen (O) was denoted at the wavelength of 777 nm. Atomic oxygen (ground/excited states) is believed to have a significant effect on cells and therefore a broad biomedical application. See, Cheng, X. et al. The effect of tuning cold plasma composition on glioblastoma cell viability. *PloS one* 9, e98652 (2014). The dominant species of the spectra in these experiments are NO or N2 lines (258, 267, 337, and 357 nm), OH (309 nm), $N_2{}^+$ (391 nm), and O (777 nm).

C. $H_2O_2$ and $NO_2{}^-$ Concentration

Figure 4A:
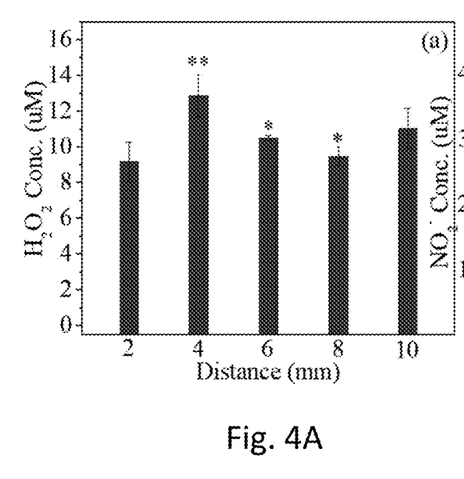
FIGS. 4A and 4B $H_2O_2$ and $NO_2^-$ concentrations in saline solution treated by plasma with self-organized pattern plasma with different air gap length (Each air gap length treated by SOP plasma for 40 seconds): (a) $H_2O_2$ concentration and (b) $NO_2^-$ concentration. Student's t-test was performed, and the significance compared to the 2 mm is indicated as *$p<0.005$, $p<0.01$, *$p<0.001$. (n=3)
Figure 4B:
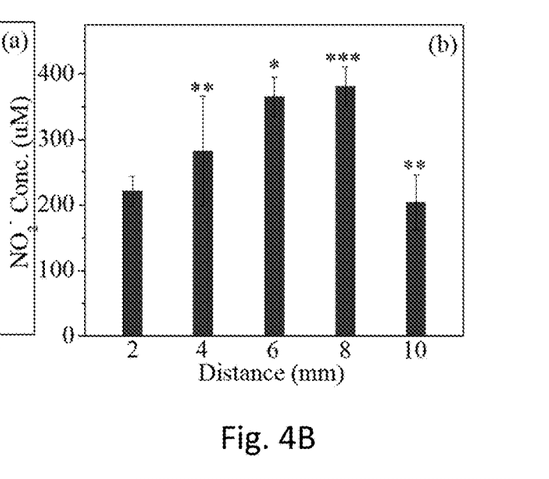

Plasma species penetrate through the plasma-liquid interface and can produce chemically reactive species in the saline solution. Complex chemistry is associated with plasma produced species in liquid. See, Chen, Z., Cheng, X., Lin, L. & Keidar, M. Cold atmospheric plasma discharged in water and its potential use in cancer therapy. *Journal of Physics D: Applied Physics* 50, 015208 (2017). These reactions lead to the formation of short- and long-lived species. $H_2O_2$ and $NO_2{}^-$ are relatively long-lived species in the plasma-activated saline solution. The air gap length dependencies of the $H_2O_2$ and $NO_2{}^-$ concentrations in the plasma-activated saline solution with gap distance as a parameter are shown in FIG. 4. The concentration of $H_2O_2$ increased initially with air gap up to 4 mm then decreased except 10 mm as shown in FIG. 4a. The concentration of $NO_2{}^-$ increases with air gap from 2 mm to 8 mm, then decreases at 10 mm.

D. Cell Viability of H6c7 and BxPC-3

Figure 5A:
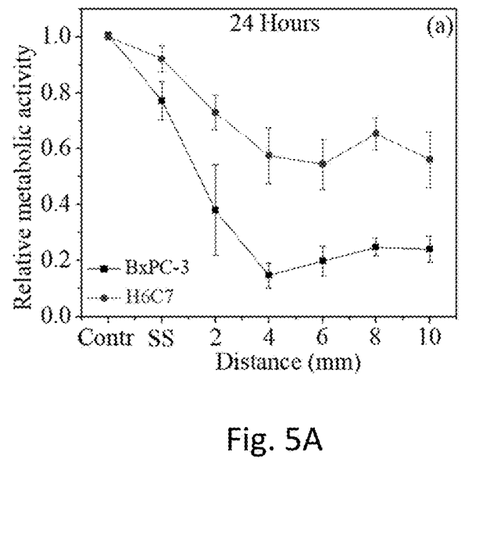
Figure 5B:
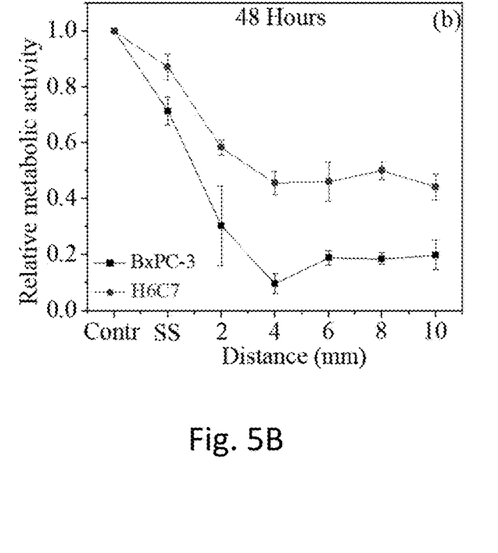

To investigate the potential of plasma-activated saline solution, we treated BxPC-3 human pancreas cancer cells and H6c7 human normal cells with them. RPMI, KSFM, and untreated saline solution were used as controls. FIG. 5 shows the cell viability of BxPC-3 human pancreas cancer cells and H6c7 human pancreas normal cells exposed to RPMI/KSFM, saline solution, and plasma-activated saline solutions for 24 h and 48 h. We can see that plasma-activated saline solutions have stronger effect on the cancer cells than that on the normal cells. For BxPC-3 cancer cells, when incubated for 24 h and 48 h, cell viability decreased firstly then increased with air gap length increasing. The minimum cell viability appears at 4 mm air gap. For H6c7 normal cells, when incubated for 24 h and 48 h, plasma with SOP at 6 mm air gap has the most significant effect of plasma-activated saline solutions.

In the past it was found that under some conditions cold atmospheric plasma can be directly applied to cancer cells without influencing the healthy tissues. Keidar, M. et al. Cold plasma selectivity and the possibility of a paradigm shift in cancer therapy. *British journal of cancer* 105, 1295-1301 (2011); Keidar, M. Plasma for cancer treatment. *Plasma Sources Science and Technology* 24, 033001 (2015); Yan, D., Sherman, J. H. & Keidar, M. Cold atmospheric plasma, a novel promising anti-cancer treatment modality. *Oncotarget* 8, 15977-15995 (2017); Karki, S. B., Thapa Gupta, T., Yildirim-Ayan, E., Eisenmann, K. M. & Ayan, H. Investigation of nonthermal plasma effects on lung cancer cells within 3D collagen matrices. *Journal of Physics D Applied Physics* 50 (2017); and Karki, S. B., Yildirim-Ayan, E., Eisenmann, K. M. & Ayan, H. Miniature Dielectric Barrier Discharge Nonthermal Plasma Induces Apoptosis in Lung Cancer Cells and Inhibits Cell Migration. *BioMed research international* 2017 (2017)

At the same time plasma-activated media have been explored and found to have a cytotoxic effect in oncology. In the above experiments, saline solutions were treated by plasma with various SOPs to be applied to human pancreatic cancer and normal cells. Discharge is formed between pin and liquid electrode and result in SOP formation dependent on discharge gap as shown in FIG. 2A.

Transport of ROS/RNS across the plasma/liquid interface is affected by SOP. As such modification of saline solution by discharge is affected and controlled by SOP at the plasma-liquid interface. Typical optical emission spectra of such plasmas at different air gap were shown in FIG. 3 indicating that plasma at each air gap length contains ROS and RNS in the gas phase. ROS and RNS were also formed in plasma-activated saline solution. RNS are well known to induce cell death via DNA double-strand breaks and apoptosis, where ROS are capable of inducing the apoptosis and necrosis. See, Boehm, D., Heslin, C., Cullen, P. J. & Bourke, P. Cytotoxic and mutagenic potential of solutions exposed to cold atmospheric plasma. *Scientific reports* 6, 21464 (2016) and Kim, S. J. & Chung, T. Cold atmospheric plasma jet-generated RONS and their selective effects on normal and carcinoma cells. *Scientific reports* 6, 20332 (2016). Our results in FIG. 4 show that the $H_2O_2$ concentration is highest at 4 mm air gap distance while $NO_2{}^-$ concentration is highest at 8 mm air gap distance. Possible reactions illustrating the routes of $H_2O_2$ and $NO_2{}^-$ formation in liquid and plasma have been reported in our previous articles[32,40,41]. See, Chen, Z., Cheng, X., Lin, L. & Keidar, M. Cold atmospheric plasma discharged in water and its potential use in cancer therapy. *Journal of Physics D: Applied Physics* 50, 015208 (2017); Chen, Z., Lin, L., Cheng, X., Gjika, E. & Keidar, M. Treatment of gastric cancer cells with nonthermal atmospheric plasma generated in water. *Biointerphases* 11, 031010 (2016); and Chen, Z., Lin, L., Cheng, X., Gjika, E. & Keidar, M. Effects of cold atmospheric plasma generated in deionized water in cell cancer therapy. *Plasma Processes and Polymers* 13, 1151-1156 (2016). From FIG. 2 Awe can see that plasma average discharge power is growing with increasing air gap, which results in the temperature of plasma-activated saline solutions going up (except 10 mm). Since $H_2O_2$ is thermodynamically unstable, its rate of decomposition increases with rising temperature. See, Goss, D. J. & Petrucci, R. H. *General Chemistry Principles & Modern Applications, Petrucci, Harwood, Herring, Madura: Study Guide*. (Pearson/Prentice Hall, 2007). It should be pointed out that the plasma discharge becomes unstable at the air gap length of about 10 mm. The discharge must be re-ignited. As such, the discharge instability at 10 mm gap might lead to a low concentration of nitrite. FIG. 5 shows that plasma-activated saline solution affects cancer and normal pancreatic cells in a selective manner. Plasma with SOP activating saline solutions have more effect on cancer cells. The trend of pancreatic normal and cancer cells can be attributed to the trend of ROS and RNS concentration with different air gap distances. On the other hand, $H_2O_2$ reacts with $NO_2^-$ to form peroxynitrite $OONO^-$ and $H_2O$. See, Tian, W. & Kushner, M. J. Atmospheric pressure dielectric barrier discharges interacting with liquid covered tissue. *Journal of Physics D: Applied Physics* 47, 165201 (2014). $ONOO^-$ is a powerful oxidant and nitrating agent that is known to be a much more damaging to cancer cells[44]. See, Beckman, J. S. & Koppenol, W. H. Nitric oxide, superoxide, and peroxynitrite: the good, the bad, and ugly. *American Journal of Physiology-Cell Physiology* 271, C1424-C1437 (1996). Therefore, a synergistic effect of ROS and RNS is suspected to play a key role in the apoptosis of the plasma solutions. For BxPC-3 cancer cells, intracellular ROS-mediated up-regulation of DR5 can leads to apoptosis (procaspase-8 is a direct downstream target of DR5). See, Kong, R. et al. Dihydroartemisinin enhances Apo2L/TRAIL-mediated apoptosis in pancreatic cancer cells via ROS-mediated up-regulation of death receptor 5. *PLoS One* 7, e37222 (2012). On the other hand, intracellular generation of ROS induces increasing protein expression of Bax, disruption of the mitochondrial membrane potential and release of cytochrome c and AIF into the cytosol resulting in to the activation of caspase9/3 cascade. See, Zhang, R., Humphreys, I., Sahu, R. P., Shi, Y. & Srivastava, S. K., "In vitro and in vivo induction of apoptosis by capsaicin in pancreatic cancer cells is mediated through ROS generation and mitochondrial death pathway," *Apoptosis* 13, 1465-1478 (2008). Therefore, plasma with SOP-induced intracellular generation of ROS induced apoptosis in BcPC-3 cancer cells might be orchestrated by the synergistic effects of both extrinsic and intrinsic pathways. The results indicate the cytotoxicity of plasma-activated saline solution is specific to pancreatic adenocarcinoma cancer cells. The plasma-activated saline solution at 4 mm air gap distance had the most significant affect in inducing cell death in pancreatic cancer cells. This is related to certain amounts of ROS and RNS generated by double ring-like structure plasma with SOPs

CONCLUSION

The above experiments demonstrate that self-organized pattern plasma-activated saline solutions applied to both BxPC-3 human pancreatic cancer and H6c7 human pancreatic normal cells exhibit selective manners. The air gap at a distance between 2 and 10 mm results into various shapes of self-organized patterns (SOPs) on saline solution anode. A synergistic effect of RNS and ROS present in the plasma solution is suspected to play a key role in the cell death. The SOP plasma-activated saline solution at 4 mm air gap distance had the most significant affect in inducing cell death in both pancreatic normal and cancer cells. The SOP plasma-activated saline solutions have more serious effect on BxPC-3 human pancreatic adenocarcinoma cancer cells than H6c7 human pancreatic epithelial normal cells. These results suggest that SOP plasma-activated saline solutions can be used with anti-tumor effect for clinical applications.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

The invention claimed is:

1. A method for manufacturing plasma-activated saline for treatment of cancer cells comprising:
   immersing a cathode in saline solution in a container;
   positioning an anode at a fixed distance from a surface of said saline solution in said container; and
   applying electrical energy to said anode for a fixed period of time;
   wherein said fixed distance and said fixed period of time are selected to cause a plasma self-organized pattern at a surface of said saline solution with an atmospheric discharge between said anode and said cathode and
   where in said plasma self-organized pattern comprises a double ring structure.

2. The method for manufacturing plasma-activated saline for treatment of cancer cells according to claim 1 wherein said fixed distance is 4-6 mm.

3. The method for manufacturing plasma-activated saline for treatment of cancer cells according to claim 1 wherein said fixed time is 40 seconds.

4. The method for manufacturing plasma-activated saline for treatment of cancer cells according to claim 1 wherein said double ring structure comprises a solid inner ring surrounded by a continuous outer ring.

5. The method for manufacturing plasma-activated saline for treatment of cancer cells according to claim 1 wherein said double ring structure comprises a solid inner ring surrounded by a discontinuous outer ring.

6. The method for manufacturing plasma-activated saline for treatment of cancer cells according to claim 1 wherein said double ring structure comprises a continuous inner ring surrounded by a continuous outer ring.

7. The method for manufacturing plasma-activated saline for treatment of cancer cells according to claim 1 wherein said double ring structure comprises a continuous inner ring surrounded by a discontinuous outer ring.

* * * * *